US00PP26796P2

(12) United States Plant Patent
Gabriel

(10) Patent No.: US PP26,796 P2
(45) Date of Patent: Jun. 7, 2016

(54) BLUEBERRY PLANT NAMED 'OBF0604'

(50) Latin Name: *Vaccinium corymbosum*
Varietal Denomination: OBF0604

(71) Applicant: Robert Gabriel, Silverton, OR (US)

(72) Inventor: Robert Gabriel, Silverton, OR (US)

( * ) Notice: Subject to any disclaimer, the term of this patent is extended or adjusted under 35 U.S.C. 154(b) by 171 days.

(21) Appl. No.: 13/998,289

(22) Filed: Oct. 17, 2013

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

PUBLICATIONS

Upov International Union for the Protection of New Varieties of Plants 2012, retrieved on Jul. 16, 2015, retrieved from the Internet at <http://www.upov.int/edocs/infdocs/en/upov_inf_12_4.pdf> pp. 1 and 4.*

* cited by examiner

*Primary Examiner* — June Hwu
(74) *Attorney, Agent, or Firm* — Klarquist Sparkman, LLP

(57) ABSTRACT

A new and distinct cultivar of Northern Highbush Blueberry plant characterized by its exceptionally high yield, concentrated ripening of the berries, very large berry size, excellent powder-blue color or "bloom" on berry, and excellent vigor. In addition the new cultivar produces mid-season, has good flavor, small, dry stem scars, a bushy habit, and can be harvested mechanically.

3 Drawing Sheets

Botanical classification: *Vaccinium corymbosum.*
Variety nomination: 'OBF0604'.

FIELD

The present invention relates to a new and distinct cultivar of Northern Highbush blueberry, or *Vaccinium corymbosum* and given the name 'OBF0604'. *Vaccinium corymbosum* is of the family Ericaceae.

BACKGROUND

Northern Highbush blueberries are the most commonly planted blueberries used for commercial and home production of fruit in the Northern U.S. and Canada. The new cultivar is from a planned breeding program for an improved blueberry. It was developed at a blueberry farm in Silverton, Oreg. using open pollination with unnamed seedlings for the parents.

This new Northern Highbush Blueberry is uniquely distinguished by its:

1. exceptionally high yield,
2. concentrated ripening of the berry,
3. very large berry size,
4. excellent powder-blue color or "bloom" on the berry,
5. and excellent vigor.

In addition the new cultivar produces mid-season, has good flavor, small, dry stem scars, a bushy habit, and can be harvested mechanically.

Compared to *Vaccinium corymbosum* 'Draper', U.S. Plant Pat. No. 15,103, the new cultivar is more vigorous, with higher yield, and a larger berry.

Compared to *Vaccinium corymbosum* '06-22' (U.S. Plant patent application Ser. No. 13/998,303), the new variety is more vigorous, wider spreading, and has a larger berry.

Compared to *Vaccinium corymbosum* '06-27' (U.S. Plant patent application Ser. No. 13/998,287), the new cultivar has a larger berry size, better yield, and a bushier habit. The new cultivar produces slightly earlier, mid-season rather than mid to late-season.

Asexual propagation by stem tip cuttings in Silverton, Oreg., shows that the foregoing characteristics and distinctions come true to form and are established and transmitted through succeeding propagations. The present invention has not been evaluated under all possible environmental conditions. The phenotype may vary with changes in environment without a change in the genotype of the plant.

SUMMARY

The foregoing and other objects, features, and advantages of the invention will become more apparent from the following detailed description, which proceeds with reference to the accompanying figures.

DETAILED DESCRIPTION

Figure 1:
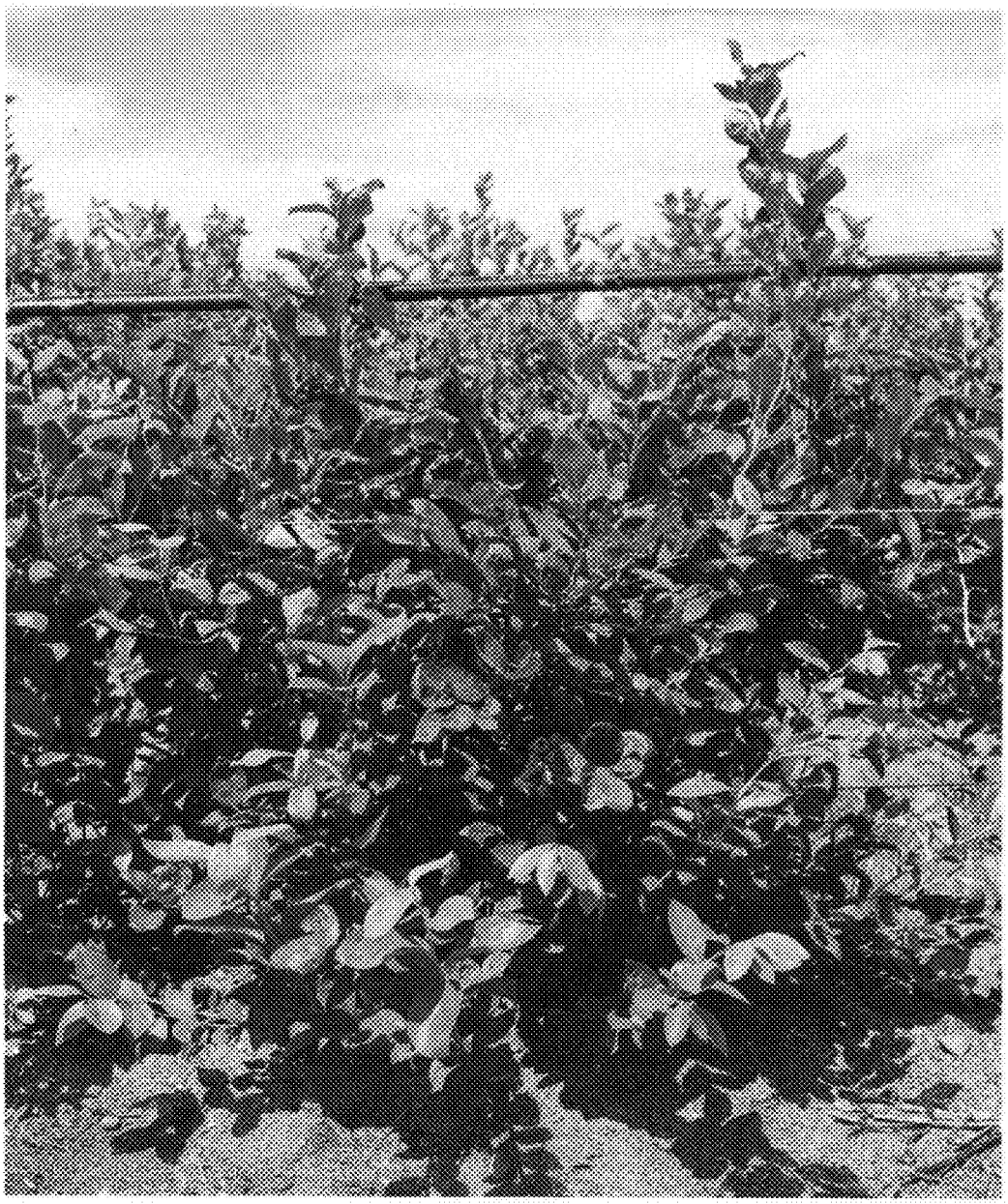
FIG. 1 shows a 3 year old plant of the new cultivar growing in the field in fruit in mid-July in Silverton, Oreg.
Figure 2:
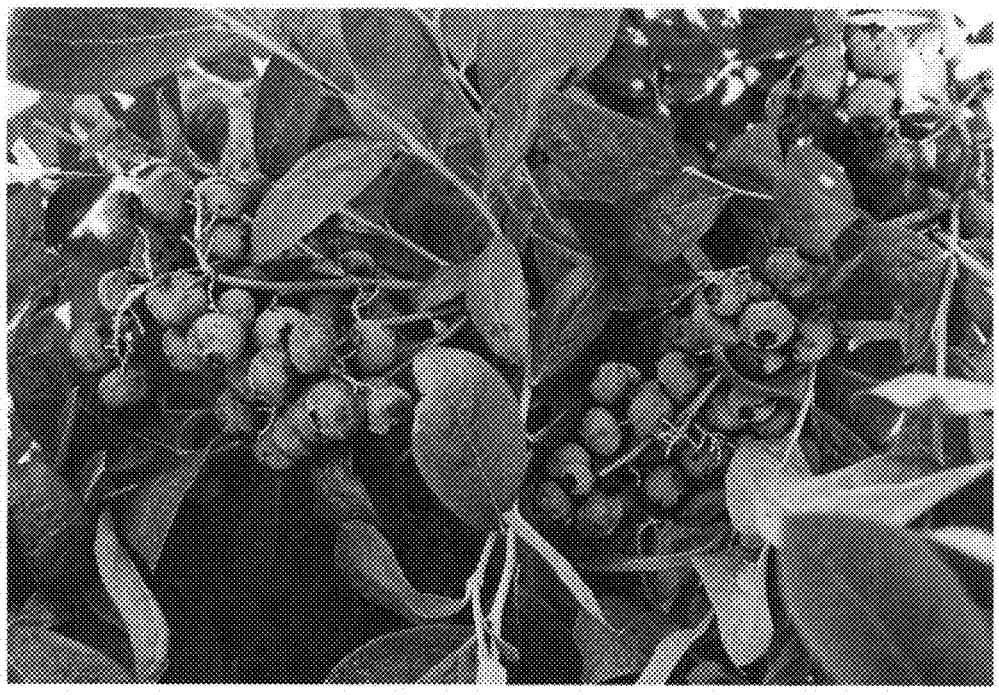
FIG.2 shows a close up of the fruit clusters of my new cultivar.
Figure 3:
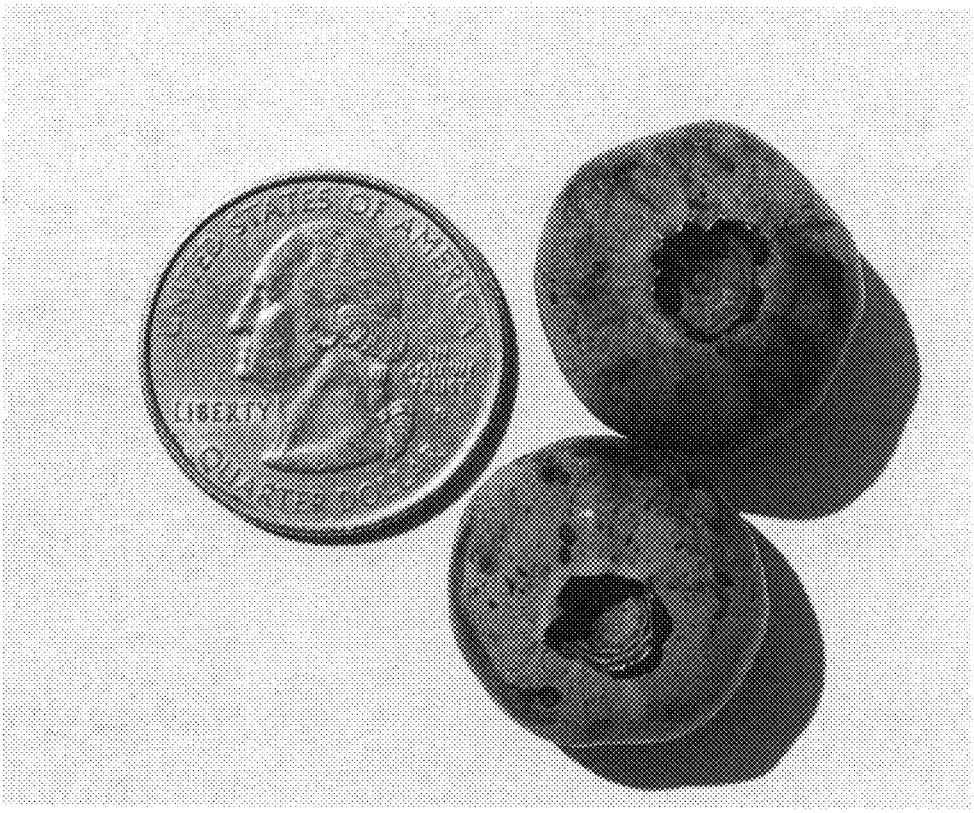
FIG. 3 shows a close up of 2 berries of my new cultivar; compared in size to the size of a US quarter.

The following is a detailed description of the new cultivar based on observations taken in mid-July of a three-year-old specimen grown in the field under average conditions in full sun in Silverton, Oreg. Silverton, Oreg. is in USDA hardiness zone 8. The color descriptions are all based on *The Royal Horticultural Society Colour Chart, 5th* edition.

Plant:

*Type*.—Deciduous shrub.

*Hardiness*.—Not yet determined, observed growing in USDA Zone 8.

*Size*.—About 104 cm tall and 170 cm wide.

*Growth habit*.—Upright, bushy.

*Productivity*.—Very high crop yields.

*Date of vegetative bud burst at time of culture*.—Second week of March in Silverton, Oreg.

*Chilling requirement*.—Expect 1000 hours.

*Vigor*.—Excellent.

Stem (cane):

*Type*.—Woody, semi-erect with excellent branching.

*Size*.—Trunk base is 4.1 cm at 1 cm above the ground, 8 mm wide at 3 year old, 4 mm wide at 2 year old, 2 to 3 mm wide at this year growth.

*# stems*.—4 to 8 main stems from the base.

*Internodes*.—1.2 to 4 cm long.

*Surface*.—Glabrous.

*Rooting*.—From current season's wood takes 60 to 90 days to root.

*Color*.—New stems to 1 year old—Yellow Green 145A, 2 to 3 year old — Brown N200B and Brown 200D.

Leaf:

*Type*.—Simple.

*Shape*.—Broadly elliptic.

*Arrangement*.—Alternate.

*Margins*.—Entire.

*Apex*.—Acute.

*Base*.—Cuneate.

*Venation*.—Pinnate, with veins Yellow Green 145C on top and 145D on bottom side.

*Blade size*.—Grows to 7.5 cm long and 4.9 cm wide.

*Surface*.—Glabrous on both sides.

*Petiole description*.—4 mm long and 1.5 mm wide, Yellow Green 145C on both sides.

*Leaf color*.—Topside N137A, bottom side closest to Greyed Green 191A.

Inflorescence:

*Type*.—Raceme or cluster, within each cluster are usually 5 groups of 8 to 11 flowers, grouped very close together.

*Dimensions of cluster*.—3.5 cm wide by 8.5 to 20 cm long.

*Number of flowers per cluster*.—About 50.

*Peduncle*.—5 cm long and 3 mm wide, glabrous, Yellow Green 145A, strongly tinted Greyed Orange 177B.

*Pedicel description*.—2 to 5 mm long, 1 mm wide, glabrous, Yellow Green 145A, tinted in sun Greyed Orange 177B.

*Bloom period*.—Mid April in Silverton, Oreg.

Flower bud:

*Size*.—11 mm long and 6 mm wide.

*Shape*.—Ovoid

*Color*.—White 155A tinted Greyed Purple 185D. .

Flower:

*Type*.—Regular, urceolate.

*Description*.—10 mm long and 9 mm wide overall; with corolla 10 mm long and 9 mm wide, 5 lobes, reniform, reflexed, 2 mm wide and 1 mm deep, entire, tip obtuse, glabrous, color inside and out White NN155A with Yellow Green 144A tints on lobes (sometimes lightly tinted Greyed Orange 177A in full sun); calyx 8 mm wide and 3 mm deep overall, 5 lobes, each 3 mm wide and 2 mm deep, broadly ovate, margins entire, tips obtuse, glabrous, color inside and outside Green 138B (outside edges tinted Greyed Orange 177A in high light); stamen 10 in a ring around the pistil, each 6 mm long, 1 mm wide, filaments 4 mm long and 1 mm wide, Yellow Green 145D, anthers 3 mm long and less than 1 mm wide, Greyed Orange 165B, pollen — none seen; 1 pistil 10 mm long and to 4 mm wide, ovary 2 mm long and 4 mm wide, Green 137A, style 8 mm long and 0.8 mm wide, Green 138A, stigma Green 137B.

*Fragrance*.—None.

Fruit (berry):

*Date of 50% maturity in Silverton, Oreg*.—Jul. 12, 2013.

*Fruiting period*.—Mid season.

*Number of bunches per plant*.—About 40.

*Berry size*.—20 mm wide and 15 mm deep.

*Berry shape*.—Oblate spheroid.

*Berry color*.—Closest to Violet Blue N92C without glaucous bloom, glaucous bloom Violet Blue 98D, flesh White 155A.

*Fruit stem scar*.—Small, 1.2 mm.

*Berry firmness*.—Firm.

*Berry flavor and texture*.—Medium.

*Berry acidity*.—Low.

*Fruit cluster density*.—Medium.

*Berry calyx basin*.—Averages 7 mm wide and 3 mm deep.

*Fruit sweetness*.—Medium.

*Pollination requirement*.—Low.

*Fruiting type*.—Fruits on one year old shoots.

*Storage quality*.—Good.

*Suitability for mechanical harvest*.—Excellent.

*Uses*.—Mechanical harvest, fresh market, home.

Seed:

*Seed abundance in fruit*.—Low, 0 to 20 per fruit.

*Seed color*.—Greyed Orange 174A.

*Seed size*.—1.0 mm long.

Pest and disease tolerance: No exceptional disease or pest resistance or susceptibility observed. Typical for mid southern highbush blueberries.

I claim:

1. A new and distinct highbush blueberry plant as herein illustrated and described.

* * * * *